US007604961B2

(12) United States Patent
Liang et al.

(10) Patent No.: US 7,604,961 B2
(45) Date of Patent: *Oct. 20, 2009

(54) VP1 OF FOOT-AND-MOUTH DISEASE VIRUS

(75) Inventors: Shu-Mei Liang, Taipei (TW);
Jeng-Hwan Wang, Taipei (TW);
Jeng-Jer Shieh, Yunlin Hsien (TW)

(73) Assignee: Academia Sinica, Taipei (TW)

( * ) Notice: Subject to any disclaimer, the term of this patent is extended or adjusted under 35 U.S.C. 154(b) by 43 days.

This patent is subject to a terminal disclaimer.

(21) Appl. No.: 11/748,294

(22) Filed: May 14, 2007

(65) Prior Publication Data

US 2008/0199911 A1    Aug. 21, 2008

Related U.S. Application Data

(62) Division of application No. 10/449,531, filed on May 29, 2003, now Pat. No. 7,217,784.

(51) Int. Cl.
*C12N 15/09* (2006.01)
*C07K 1/00* (2006.01)
*C07K 1/02* (2006.01)
*C07K 1/14* (2006.01)
*C07K 1/36* (2006.01)

(52) U.S. Cl. ........................................ 435/69.3; 530/417

(58) Field of Classification Search ............... 424/216.1
See application file for complete search history.

(56) References Cited

U.S. PATENT DOCUMENTS 4,511,503 A * 4/1985 Olson et al. ............... 530/422
4,620,948 A * 11/1986 Builder et al. ............. 530/419
4,769,237 A * 9/1988 Bittle et al. ............... 424/186.1

OTHER PUBLICATIONS

Knowles N. J. et al., "Emergence in Asia of Foot-and-Mouth Diseases Viruses with Altered Host Range: Characterization of Alterations in the 3A Protein," *J. Virol.* 74: 1551-1556 (2001).
NBI Accession No. AJ294924 (2001).
Rueckert, Picornaviridae: The Viruses and Their Replication. In B.N. Fields et al. (ed.), Fields Virology, 3rd ed. Philadelphia: Lippencott-Raven Publishers; 1995 615.
N. R. Parry et al. "Neutralizing Epitopes of Type O Foot-and-Mouth Disease Virus. II. Mapping Three Conformational Sites with Synthetic Peptide Reagents". J. Gen. Virol. 70:1493-1503, 1989.
D. McCahon et al. "Evidence for At Least Four Antigenic Sites on Type O Foot-and-Mouth Disease Virus Involved in Neutralization; Identification by Single and . . . ". J. Gen. Virol. 70:639-645, 1989.
A. Villaverde et al. "A recombinant, arginine-glycine-aspartic acid (RGD) motif from foot-and-mouth disease virus binds mammalian cells through vitronectin and . . . ". Gene 180:101-106, 1996.
T. Jackson et al. "Efficient Infection of Cells in Culture by Type O Foot-and-Mouth Disease Virus Requires Binding to Cell Surface Heparan . . . ". Journal of Virology 70(8):5282-5287, Aug. 1996.

K. Strebel et al. "Characterization of Foot-and-Mouth Disease Virus Gene Products with Antisera Against Bacterially Synthesized Fusion Proteins". Journal of Virology 57(3):983-991, Mar. 1986.
D. Kleid et al. "Cloned Viral Protein Vaccine for Foot-and-Mouth Disease: Responses in Cattle and Swine". Science 214:1125-1129, Dec. 1981.
J. Chinsangaram et al. "Antibody Response in Mice Inoculated with DNA Expressing Foot-and-Mouth Disease Virus Capsid Proteins". Journal of Virology 72(5):4454-4457, May 1998.
K. Bayry et al. "Immuno affinity purification of foot and mouth disease virus type specific antibodies using recombinant protein . . . ". Journal of Virological Methods 81:21-30, 1999.
V.V.S. Suryanarayana et al. "Characterization and Immune Response of a Protein Produced by a cDNA Clone of Foot and Mouth . . . ". Biochemistry International 26(6):1003-1016, May 1992.
V.D. Murdin et al. "Isolation of Capsid Proteins of Foot-and-Mouth Disease Virus by Chromatofocusing". Journal of Virological Methods 207-216, 1983.
C.-C. Huang et al. "Anti-3AB antibodies in the Chinese yellow cattle infected by the O/Taiwan/99 foot-and-mouth disease virus". Veterinary Microbiology 84:317-326, 2002.
M. Agterberg et al. "Protection of guinea-pigs against foot-and-mouth disease virus by. immunization with a PhoE-FMDV hybrid protein". Vaccine 8:438-440, Oct. 1990.
T. Haack et al. "A cyclic disulfide peptide reproduces in solution the main structural features of a native antigenic . . . ". International Journal of Biological Macromolecules 20:209-219, 1997.
E. Domingo et al. "Biochemical and structural studies with neutralizing antibodies raised against foot-and-mouth disease virus". Virus Research 62:169-175, 1999.
A. Berinstein et al. "Antibodies to the Vitronectin Receptor (Integrin $\alpha_v\beta_3$) Inhibit Binding and Infection of Foot-and-Mouth Disease . . . " Journal of Virology 69(4):2664-2666, Apr. 1995.
N. Parry et al. "Structural and serological evidence for a novel mechanism of antigenic variation in foot-and-mouth disease virus". Letters to Nature 347:569-572, Oct. 11, 1990.
D. Logan et al. "Structure of a major immunogenic site on foot-and-mouth disease virus". Letters to Nature 362:566-568, Apr. 8, 1993.
E. Fry et al. "The structure and function of a foot-and-mouth disease virus-oligosaccharide receptor complex". EMBO Journal 18(3):543-554, 1999.

(Continued)

*Primary Examiner*—Mary E Mosher
*Assistant Examiner*—Myron G Hill
(74) *Attorney, Agent, or Firm*—Occhiuti Rohlicek & Tsao LLP

(57) ABSTRACT

A pure, water-soluble polypeptide containing one or more monomers of a VP1 protein of a foot-and-mouth disease virus; or a pure, water-insoluble polypeptide comprising two or more monomers of a VP1 protein of a foot-and-mouth disease virus. Also disclosed are a vaccine containing the polypeptide, a method of producing the polypeptide, and a method of inducing an immune response in a subject by administering to the subject an effective amount of the polypeptide.

4 Claims, No Drawings

OTHER PUBLICATIONS

C. Carrillo et al. "Protective Immune Response to Foot-and-Mouth Disease Virus with VP1 Expressed in Transgenic Plants". Journal of Virology 72(2):1688-1690, Feb. 1998.

R. DiMarchi et al. "Protection of Cattle Against Foot-and-Mouth Disease by a Synthetic Peptide". Science 232:639-641, May 2, 1986.

A. Wigdorovitz et al. "Induction of a Protective Antibody Response to Foot and Mouth Disease Virus in Mice Following Oral or Parenteral Immunization . . . " Virology 255:347-353, 1999.

A. Wigdorovitz et al. "Protection of Mice against Challenge with Foot and Mouth Disease Virus (FMDV) by Immunization with Foliar Extracts from Plants Infected . . . " Virology 264:85-91, 1999.

T. Jackson et al. "Arginine-Glycine-Aspartic Acid-Specific Binding by Foot-and-Mouth Disease Viruses to the Purified Integrin $\alpha_v\beta_3$ In Vitro". Journal of Virology 71(11):8357-8361, Nov. 1997.

R. Acharya et al. "The three-dimensional structure of foot-and-mouth disease virus at 2.9 Å resolution". Nature 337:709-716, Feb. 12, 1989.

S. Lea et al. "The structure and anigenicity of a type C foot-and-mouth disease virus". Structure 2:123-139, Feb. 15, 1994.

J. Kluger. "Keep Foot-and-Mouth Disease Out of America: Crackdown on a Virus". Time 36-37, Mar. 26, 2001.

G. de Prat-Gay. "Conformational Preferences of a Peptide Corresponding to the Major Antigenic Determinant of Foot-and-Mouth Disease Virus: Implications for Peptide Vaccine Approaches". Archives of Biochemistry and Biophysics 341(2):360-369, 1997.

A. Benito et al. "Improved Mimicry of a Foot-and-Mouth Disease Virus Antigenic Site by a Viral Peptide Displayed . . . " Biotechnology 13:801-802, Aug. 13, 1995.

D. M. Moore et al. "Identification of virus neutralizing epitopes on naturally occurring variants of type $A_{12}$ foot-and-mouth disease virus". Virus Research 14:281-296, 1989.

S. J. Cox et al. "Emergency vaccination of sheep against foot-and-mouth disease: protection against disease and reduction in contact transmission". Vaccine 17:1858-1868, 1999.

D. M. Perez Filgueira et al. "Effect of *Mycobacterium* sp. Wall and Avridine on the antibody response, IgG isotype profile and proliferative response induced . . . ". Vaccine 17:345-352, 1999.

D. M. Perez Filgueira et al. "Effect of *Mycobacterium* sp. Wall and Avridine on the antibody response, IgG isotype profile and proliferative response . . . ".Vaccine 17:345-352, 1999.

A. Berinstein et al. "Protective immunity against foot-and-mouth disease virus induced by a recombinant vaccinia virus". Vaccine 18:2231-2238, 2000.

A. V. Iyer et al. "Evaluation of three 'ready to formulate' oil adjuvants for foot-and-mouth disease vaccine production". Vaccine 19:1097-1105, 2001.

J. Ignacio Nunez et al. "A Single Amino Acid Substitution in Nonstructural Protein 3A Can Mediate Adaptation of Foot-and-Mouth . . . ". Journal of Virology 75(8):3977-3983. Apr. 2001.

C. M. Ruiz-Jarabo et al. "Antigenic properties and population stability of a foot-and-mouth disease virus with an altered Arg-Gly-Asp . . . ". Journal of General Virology 80:1899-1909, 1999.

F. Sobrino et al. "Antigenic variation of foot-and-mouth disease virus of serotype C during propagation in the field is mainly restricted to only one . . . " Virus Research 14:273-280, 1989.

C. Carrillo et al. "Protective Immune Response to Foot-and-Mouth Disease Virus with VP1 Expressed in Transgenic Plants". Journal of Virology 72(2):1688-1690, Feb. 1998.

A. Haghparast et al. "Selection of T-cell epitopes from foot-and-mouth disease virus reflects the binding affinity to different cattle MHC class II molecules", Immunogenetics 51:733-742, 2000.

A. Sharma et al. "Specific Interactions between Human Integrin $\alpha_v\beta_3$ and Chimeric Hepatitis B Virus Core Particles Bearing the Receptor-Binding Epitope . . . ". Virology 239:150-157, 1997.

M. G. Mateu et al. "Systematic Replacement of the Amino Acid Residues within an Arg-Gly-Asp-containing Loop of Foot-and- . . . " Journal of Biological Chemistry 271(22):12814-12819, 1996.

W. F. Ochoa et al. "A multiply substituted G-H loop from foot-and-mouth disease virus in complex with a neutralizing antibody: a role for water . . . ". Journal of General Virology 81:1495-1505, 2000.

D. Haydon et al. "Characterizing Sequence Variation in the VP1 Capsid Proteins of Foot and Mouth Disease Virus (Serotype 0) with Respect to Virion Structure". J Mol Evol 46:465-475, 1998.

M. Leippert et al. "Point Mutations within the $\beta G$-$\beta H$ Loop of Foot-and-Mouth Disease Virus $O_1K$ Affect Virus Attachment to Target Cells". Journal of Virology 71(2):1046-1051, Feb. 1997.

T. St.C. McKenna et al. "Strategy for producing new foot-and-mouth disease vaccines that display complex epitopes". Journal of Biotechnology 44:83-89, 1996.

J. Huang et al. "Recombinant Fusion Protein and DNA Vaccines Against Foot and Mouth Disease Virus Infection in Guinea Pig and Swine". Virol Immunology 12(1):1-8, 1999.

C.-P. Tsai et al. "Molecular epidemiological studies on foot-and-mouth disease type O Taiwan virus from the 1997 epidemic". Veterinary Microbiology 74:207-216, 2000.

J.-J. Shieh et al. "Enhancement of the immunity to foot-and-mouth disease virus by DNA priming and protein boosting immunization". Vaccine 19:4002-4010, 2001.

V.V.S. Suryanarayana et al. "*E.coli* expressed proteins as diagnostic reagents for typing of foot-and-mouth disease virus". Arch Virol 144:1701-1712, 1999.

O. Taboga et al. "A Large-Scale Evaluation of Peptide Vaccines against Foot-and-Mouth Disease: Lack of Solid Protection in Cattle . . . ". Journal of Virology 71(4):2606-2614, Apr. 1997.

P.I. Zamorano et al. "Induction of anti foot and mouth disease virus T and B cell responses in cattle immunized with a peptide representing ten amino acids of VP1". Vaccine 16(6):558-563, 1998.

C.Y. Wang et al. "Synthetic Peptide-based Vaccine and Diagnostic System for Effective Control of FMD". Biologicals 29:221-228, 2001.

P. Zamorano et al. "A 10-Amino-Acid Linear Sequence of VP1 of Foot and Mouth Disease Virus Containing B- and T-Cell Epitopes Induces Protection in Mice". Virology 212:614-621, 1995.

\* cited by examiner

VP1 OF FOOT-AND-MOUTH DISEASE VIRUS

CROSS-REFERENCE TO RELATED APPLICATIONS

This application is a divisional of U.S. patent application Ser. No. 10/449,531, filed May 29, 2003 and now issued as U.S. Pat. No. 7,217,784, the content of which is incorporated herein by reference.

BACKGROUND

Foot-and-mouth disease virus (FMDV), the etiological agent of foot-and-mouth disease (FMD), is a constant threat to domestic livestock throughout the world. FMDV belongs to the aphthovirus genus of the family Picornaviridae. Its viral particle contains a single-stranded RNA genome within an icosahedral capsid consisting of 60 copies of each of four proteins, VP1, VP2, VP3 and VP4. The particle shell is made of the three larger structural proteins, VP1 to VP3, while the smaller VP4 is located internally (Acharya et al. (1989) Nature 337(6209): 709-716).

SUMMARY

This invention relates to protecting animals from infection by foot-and-mouth disease virus using a pure VP1 polypeptide.

In one aspect, the invention features a pure, water-soluble polypeptide containing one or more monomers of a VP1 protein of a foot-and-mouth disease virus. A "pure" polypeptide is a polypeptide free from other biological macromolecules and at least 65% (i.e., any percent between 65% and 100%) pure by dry weight. The purity of a polypeptide can be measured by any appropriate standard method, for example, by column chromatography, polyacrylamide gel electrophoresis, or HPLC analysis. The VP1 protein can be a naturally occurring polypeptide, a recombinant polypeptide, or a synthetic polypeptide. Variants of a wild-type VP1 protein (e.g., a fragment of the wild-type VP1 protein) that maintain the biological activity of a wild-type VP1 protein are within the scope of the invention. One example of a polypeptide of the invention is a polypeptide that contains two monomers of a VP1 protein, i.e., a dimer. The monomers can be linked, e.g., by a disulfide bond.

In another aspect, the invention features a pure, water-insoluble polypeptide containing two or more monomers of a VP1 protein of a foot-and-mouth disease virus. The monomers are linked, e.g., by a disulfide bond.

A polypeptide of the invention can be used for generating antibodies, detecting virus infection, and producing vaccines. A vaccine of the invention contains a pharmaceutically acceptable carrier and an effective amount of a polypeptide of the invention.

The invention further features a method of producing a water-soluble polypeptide. The method involves unfolding a water-insoluble polypeptide that contains one or more monomers of a VP1 protein of a foot-and-mouth disease virus and refolding the polypeptide. For example, the water-insoluble polypeptide can be unfolded by dissolving it in a solution containing urea. The unfolded polypeptide can then be refolded, e.g., by treating it with sodium dodecyl sulfate followed by gel filtration column chromatography.

The invention also features a method of producing a polypeptide. The method involves expressing in a cell a water-insoluble polypeptide that contains two or more monomers of a VP1 protein of a foot-and-mouth disease virus and collecting the polypeptide from the cell. To facilitate collection of the polypeptide, the polypeptide can be dissolved in a solution containing urea.

In addition, the invention features a method of inducing an immune response in a subject. The method involves administering to a subject in need thereof an effective amount of a polypeptide of the invention. This method is useful for generating antibodies to VP1 and protecting a subject from infection by foot-and-mouth disease virus.

An "effective amount" is an amount of a polypeptide of the invention that is capable of producing a desirable result, e.g., generation of antibodies or protection against FMDV infection, in a subject.

The details of one or more embodiments of the invention are set forth in the accompanying description below. Other features, objects, and advantages of the invention will be apparent from the detailed description, and from the claims.

DETAILED DESCRIPTION

This invention is based on the unexpected discovery that water-soluble VP1 can be prepared by unfolding and refolding the protein. It was also discovered unexpectedly that dimeric VP1 has better thermo-stability than monomeric VP1 in retaining its antigenicity. The isolated VP1, either monomeric or dimeric, was found to be effective in eliciting neutralizing antibodies to VP1 and protecting animals from FMDV infection.

Accordingly, the invention features a pure, water-soluble polypeptide containing one or more monomers of a VP1 protein of a foot-and-mouth disease virus. The polypeptide can be prepared, e.g., according to the method described in the examples below, or by any other equivalent methods known in the art.

For example, a VP1 gene can be cloned into a vector and expressed in a cell. When an *E. coli* cell is used, the VP1 protein is expressed as inclusion bodies. The water-insoluble VP1 protein can be solubilized in a buffer solution containing 8 M urea. To prepare water-soluble VP1 protein, the solublized protein can then be purified by chromatography in the presence of 8 M urea. The unfolded protein can be refolded by passing through a gel filtration column in the presence of SDS. Water-insoluble VP1 can be encapsulated using, e.g., microsperes. Multimeric VP1 can be prepared by isolating naturally occurring multimers or by linking VP1 monomers, e.g., with oxidants.

A polypeptide of the invention can be used to generate antibodies against VP1. The VP1 antibodies can, in turn, be used in diagnosis of FMD and in evaluation of the effectiveness of medical treatments of FMD by any therapeutic approaches, e.g., by detecting the presence of the virus in a sample prepared from a subject.

Methods of making monoclonal and polyclonal antibodies and fragments thereof are known in the art. See, for example, Harlow and Lane, (1988) Antibodies: A Laboratory Manual, Cold Spring Harbor Laboratory, New York. In particular, various host animals can be immunized by injection of a composition containing a polypeptide of the invention. Host animals can include rabbits, mice, guinea pigs, pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, and dinitrophenol.

Antibodies include polyclonal antibodies, monoclonal antibodies, chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the polypeptides described above and standard hybridoma technology. Such antibodies can be of any immunoglobulin class including IgG, IgM, IgE, IgA, IgD and any subclass thereof. The hybridoma producing the Mab may be cultivated in vitro or in vivo. The ability to produce high titers of mAbs in vivo makes this an excellent method of production.

In addition, techniques developed for the production of chimeric antibodies by splicing genes from an antibody molecule of one animal species with appropriate antigen specificity together with genes from an antibody molecule of another animal species with appropriate biological activity can be used. A chimeric antibody is a molecule in which different portions are derived from different animal species, such as those having a variable region derived from a Mab of one animal species and an immunoglobulin constant region of another animal species.

Alternatively, techniques described for the production of single chain antibodies can be adapted to produce single chain antibodies against VP1. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments.

A polypeptide of the invention can also be used to produce vaccines for protecting animals against FMDV infection. Such vaccines can be prepared, e.g., according to the method described in the examples below, or by any other equivalent methods known in the art.

A vaccine of the invention contains an effective amount of a polypeptide of the invention, and a pharmaceutically acceptable carrier such as phosphate buffered saline or a bicarbonate solution. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, immune-stimulating complex (IS-COM), or immunostimulatory sequences oligodeoxynucleotides (ISS-ODN), can also be included in a vaccine of the invention, if necessary.

A subject susceptible to FMDV infection can be identified and administered with a vaccine of the invention. The dose of the vaccine depends, for example, on the particular polypeptide, whether an adjuvant is co-administered with the polypeptide, the type of adjuvant co-administered, the mode and frequency of administration, as can be determined by one skilled in the art. Administration is repeated as necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the vaccine against the VP1 protein or FMDV infection. Methods of assaying antibodies or cytotoxic T cells against the VP1 protein or FMDV infection are well known in the art. Additional boosters can be given as needed. By varying the amount of polypeptide, the dose of the vaccine, and frequency of administration, the immunization protocol can be optimized for eliciting a maximal immune response.

Before administering a vaccine of the invention in a large scale, toxicity and efficacy testings are desirable. In an example of efficacy testing, a subject can be vaccinated via an oral or parenteral route with a vaccine of the invention. After the initial vaccination or after optional booster vaccinations, the subject and a corresponding control subject receiving mock vaccinations are challenged with an $LD_{95}$ dose of FMDV. End points other than lethality can also be used. Efficacy is determined if the subject receiving the vaccine dies at a rate lower than the mock-vaccinated subject. The difference in death rates should be statistically significant.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

Expression of VP1 in *E. coli*

The VP1 gene was amplified by PCR from the plasmid pIBSY1-VP1 (Shieh et al. (2001) Vaccine 19(28-29): 4002-4010) with 5'-GTGATGCTCGAGCAGAAGC TGTTTTGCGGGT-3' (SEQ ID NO:4) and 5'-CCGGGATC-CACCACCTCTGCG GGTGACT-3' (SEQ ID NO:5) as the primers, which introduced a BamH I site at the N-terminus and an Xho I site at the C-terminus, respectively. To facilitate the purification and assay of the recombinant *E. coli*-derived VP1 (rVP1), a T7 tag and a His tag were attached to the N-terminus and the C-terminus of the VP1 gene, respectively. After restriction enzyme digestion, the amplified gene was ligated between the BamH I and the Xho I sites of pET24a(+) (Novagene, Wis.) and transformed into NovaBlue competent cells. The identified positive clones were sequenced by the Sanger dideoxy method (Sanger et al. (1977) Proc. Natl. Acad. Sci. USA 74(12): 5463-5467) on an ABI 377 autosequencer. Plasmid pVP1/Q15, isolated from one of the positive clones, was used to transform *E. coli* BL21(DE3) competent cells. The bacteria were cultured at 37° C. in an incubator-shaker until the $OD_{600}$ measurement of the cell density reached 0.6. Expression was induced by addition of isopropyl-β-D-thiogalactopyranoside (IPTG) to a final concentration of 1 mM, and the cells were grown for another 3 h before harvesting. The VP1 nucleic acid (SEQ ID NO:1), and amino acid sequences (SEQ ID NO:2) in pVP1/Q15 are shown below. The complementary strand is also shown (SEQ ID NO:3):

```
VP1 Nucleic Acid (SEQ ID NO. 1)
5'-ATGGCTAGCA TGACTGGTGG ACAGCAAATG GGTCGCGGAT

CCACCACCTC TGCGGGTGAG TCTGCGGACC CCGTGACTGC

CACCGTCGAG AACTACGGTG GTGAGACACA AGTCCAGAGG

CGCCAGCACA CGGACAGTGC GTTCATATTG GACAGGTTCG
```

-continued

```
TGAAAGTCAA GCCAAAGGAA CAAGTTAATG TGTTGGACCT

GATGGAGATC CCTGCCCACA CCTTGGTAGG GGCGCTCCTG

CGAACGGCCA CCTACTACTT CTCTGACCTG GAGCTGGCCG

TCAAGCACGA GGGCGATCTC ACCTGGGTCC CAAACGGCGC

CCCTGAGACA GCACTGGACA ACACTACCAA CCCAACAGCT

TACCACAAGG AACCCCTCAC ACGGCTGGCG CTGCCTTACA

CGGCTCCACA CCGTGTCTTA GCGACCGTCT ACAACGGGAG

CAGTAAGTAC GGTGACACCA GCACTAACAA CGTGAGAGGT

GACCTTCAAG TGTTAGCTCA GAAGGCAGAA AGAACTCTGC

CTACCTCCTT CAACTTCGGT GCCATCAAGG CAACTCGTGT

TACTGAACTA CTCTACAGAA TGAAGAGAGC CGAGACATAC

TGTCCCAGGC CCCTTCTCGC CATTCAACCG AGTGACGCTA

GACACAAGCA GAGGATTGTG GCACCCGCAA AACAGCTTCT

GCTCGAGCAC CACCACCACC ACCAC
```

VP1 Amino Adid Sequence (SEQ ID NO. 2)

```
M A S M T G G Q Q M G R G S T T

S A G E S A D P V T A T V E N Y

G G E T Q V Q R R Q H T D S A F

I L D R F V K V K P K E Q V N V

L D L M Q I E A H T L V G A L L

R T A T Y Y F S D L E L A V K H

E G D L T W V P N G A P E T A L

D N T T N P T A Y H K E P L T R

L A L P Y T A P H R V L A T V Y

N G S S K Y G D T S T N N V R G

D L Q V L A Q K A E R T L P T S

F N F G A I K A T R V T E L L Y

R M K R A E T Y C P R P L L A I

Q P S D A R H K Q R I V A P A K

Q L L L E H H H H H H
```

Complementary Sequence to SEQ ID NO. 1 (SEQ ID No. 3; from 5'-3')

```
3'-TACCGATCGT ACTGACCACC TGTCGTTTAC CCAGCGCCTA

GGTGGTGGAG ACGCCCACTC AGACGCCTGG GGCACTGACG

GTGGCAGCTC TTGATGCCAC CACTCTGTGT TCAGGTCTCC

GCGGTCGTGT GCCTGTCACG CAAGTATAAC CTGTCCAAGC

ACTTTCAGTT CGGTTTCCTT GTTCAATTAC ACAACCTGGA

CTACGTCTAG GGACGGGTGT GGAAOCATCC CCGCGAGGAC

GCTTGCCGGT GGATGATGAA GAGACTGGAC CTCGACCGGC

AGTTCGTGCT CCCGCTAGAG TGGACCCAGG GTTTGCCGCG

GGGACTCTGT CGTGACCTGT TGTGATGGTT GGGTTGTCGA

ATGGTGTTCC TTGGGGAGTG TGCCGACCGC GACGGAATGT
```

-continued

```
GCCGAGGTGT GGCACAGAAT CGCTGGCAGA TCTTGCCCTC

GTCATTCATG CCACTGTGGT CGTGATTGTT GCACTCTCCA

CTGGAAGTTC ACAATCGAGT CTTCCGTCTT TCTTGAGACG

GATGGAGGAA GTTGAAGCCA CGGTAGTTCC GTTGAGCACA

ATGACTTGAT GAGATGTCTT ACTTCTCTCG GCTCTGTATG

ACAGGGTCCG GGGAAGAGCG GTAAGTTGGC TCACTGCGAT

CTGTGTTCGT CTCCTAACAC CGTGGGCGTT TTGTCGAAGA

CGAGCTCGTG GTGGTGGTG-5'
```

Refolding and Purification Procedures

Recombinant VP1 was isolated by resuspending the bacterial cells and breaking them up with a Microfluidizer (M-110Y Cell Disruption) in TEN buffer (50 mM Tris-HCl, pH 8.0, 1 mM EDTA, 0.1 M NaCl) in an approximate ratio of 1:30 (w/v). The resultant cell lysate was centrifuged, and the pellet was washed three times with 0.5% deoxycholate in TEN buffer followed by three rinses with TEN buffer. The protein was solubilized by resuspending the pellet in freshly prepared binding buffer (20 mM Tris-HCl, pH 7.9, 0.5 M NaCl, 8 M urea). The solution was applied to a metal chelating affinity column (5×7.6 cm, Chelating Sepharose Fast Flow, Amersham Pharmacia Biotech). After washing with 2-bed volumes of binding buffer, the protein was eluted with imidazole at a gradient of 0-0.2 M. The fractions containing the rVP1 protein were collected and SDS was then added until it reached a final concentration of 1%. The protein solution was subsequently applied to a Superdex 200 column (2.6×85 cm), which was previously equilibrated with a buffer solution containing 25 mM Tris-HCl, pH 8.0, 1 mM EDTA, 0.1 M NaCl, and 0.05% SDS (TENS). Fractions containing rVP1 protein were identified by SDS-PAGE and pooled. The pooled fractions were then passed through a detergent removing column (Extracti-Gel$^R$, Pierce, Ill.) to remove SDS according to the manufacturer's recommendation.

Synthetic Peptide

A polypeptide P-29 (NGSSKYGDTSTNNVRGDLQVLAQKAERTL (SEQ ID NO:6)), representing the amino acid residues 131-159 of VP1 of the FMDV O/Taiwan/97 strain, was synthesized using an ABI peptide synthesizer and Fmoc chemistry. Its amino acid sequence was verified by mass spectrometry and amino acid composition analysis.

ELISA

ELISA was used to measure antibody titer and antigenicity. It was performed as described previously (Shieh et al. (2001) Vaccine 19(28-29): 4002-4010) with minor modifications. In brief, after formation of the plate-bound antigen-antibody complexes, the plates were washed three times with phosphate-buffered saline (PBS) containing 0.1% Tween-20 (PBST), and treated with a suitable concentration of biotinylated secondary antibodies for 1 h at 37° C. Subsequently, the plates were washed and streptavidin-peroxidase (1:3000 dilution) was added to the plates. After incubation for 1 h at room temperature, the plates were washed again. Enzyme substrate 3,3',5,5'-tetramethylbenzidine (Sigma) was then added, and the reaction was carried out at room temperature for 10 min. Finally, an equal volume of 1 $NH_2SO_4$ was added to stop the reaction and the absorbance at 450 nm was measured by an ELISA reader.

S-carboxymethylation of rVP1

DTT was added to 1 mg/ml of rVP1 in TENS buffer and adjusted to the concentration of 10 mM. The reaction was allowed to proceed for 4 h at room temperature. Then, 20 μL of freshly prepared 1 M iodoacetic acid was added to each ml of the protein solution. The mixture was kept at dark for 30 min. To quench the reaction, 1 M DTT was added until the solution reached the final concentration of 40 mM DTT. The protein solution was then dialyzed at room temperature against two changes of TENS buffer and stored at 4° C.

Assay of Thermal Influence on Antigenicity of rVP1

Influence of thermal treatment on rVP1 was determined by ELISA. In brief, mouse anti-HisTag IgG was coated onto microtiter plates. The rVP1 heated at 39, 48, 57, 66, and 75° C. for 30 min then cooled at 4° C. overnight was added to the plates and incubated for 1 h at 37° C. The bound rVP1 was detected by ELISA using swine anti-rVP1 IgG as the primary antibody and biotinylated goat anti-swine IgG as the secondary antibody. The relative antigenic activity is defined as the ratio of the absorbance of the reaction of heat-denatured antigen divided by the absorbance of the reaction of untreated antigen.

Assay for Neutralizing Antibodies

The procedure was the same as described previously (Shieb et al. (2001) Vaccine 19(28-29): 4002-4010). In brief, sera from test animals were inactivated at 56° C. for 30 min. The serum sample or control serum (50 μl) was added to the well at the end of each row of a 96-well tissue culture plate, and then diluted in a two-fold serial dilution across the plates. Fifty microliters of a 100 $TCID_{50}$ virus suspension were added to each well, and then the plate was vortexed for 1 min. After incubation at 37° C. in 5% $CO_2$ for 90 min, 100 μl of BHK-21 cell suspension ($10^6$ cells/ml) in Eagle's MEM containing 8% fetal bovine serum were added to each well. Titers were determined after 48-h incubation at 37° C. in a water-saturated atmosphere with 5% $CO_2$ and expressed as the final dilution of serum present in the serum/virus mixture at the 50% end-point. Non-paired T test was used to analyze the significance of the difference in the antibody titers.

T Cell Proliferation Assay

To determine whether rVP1 injection stimulated T cell response, T cell proliferation assay was performed. T cells from buffer control and rVP1-immunized groups of swine were enriched and purified by 1.077 g/ml Ficoll-Plaque PLUS solution (Pharmacia), respectively. T cells from each group ($5\times10^6$ cell/ml) were grown in a 96-well plate and stimulated by rVP1 (5, 10 or 20 μg/ml). The plate was incubated at 37° C. for 4 days followed by incubation for 4 h at 37° C. with 10 μl/well of BrdU labeling solution (10 mM in PBS, pH 7.4; Roche cell proliferation ELISA, colorimetric kit). The procedure for colorimetric detection was performed according to the manufacturer's instruction.

Immunization and Viral Challenge in Swine

Groups of four specific pathogen-free (SPF) swine (3-month-old, weighing approximately 25 kg), castrated male or female obtained in Taiwan, were injected intramuscularly (i.m.) at the neck with either monomeric or dimeric rVP1 emulsified with equal volumes of complete Freund's adjuvant for priming (3 mg/swine). Two swine received an injection of buffer as negative controls. Booster injection with 2 mg/swine, emulsified with Montanide ISA 206 (Seppic, France) adjuvant, was given on day 28 and 56. Sera were collected for analysis from the immunized animals on days 0, 42, and 77. Three weeks after the second booster, all swine were challenged with 0.5 ml of $10^5$ $TCID_{50}$ of FMDV O/Taiwan/97 by injection into the right front heel bulb. The swine were monitored for signs of FMD for 14 days. The signs included elevation of body temperatures above 40° C. for three successive days, lameness, vesicular lesions on the snout, and the coronary bands of the legs.

Results

Expression, Isolation and Refolding of rVP1

The VP1 gene of 0 type FMDV (O/Taiwan/97) from infected pigs in Taiwan was expressed in *E. coli* using the pET expression system. The recombinant VP1 (rVP1) that expressed exclusively as inclusion bodies was solubilized in a buffer solution containing 8 M urea. The extracted rVP1 was then purified by one-step metal chelating affinity chromatography in the presence of 8 M urea. Attempts to refold rVP1 by dialysis against various buffer solutions or distilled water all resulted in the precipitation of this protein. To circumvent the solubility problem, a refolding procedure using SDS to assist protein refolding was subsequently performed in a gel filtration column. Two major fractions, namely peaks A and B, were eluted from a Superdex-200 column chromatography.

Densitometric analysis of SDS PAGE revealed that the expression level of the rVP1 was about 6% of total *E. coli* proteins. The induced rVP1 could be greater than 90% pure after one-step metal chelating affinity chromatography. The apparent relative molecular weights of peak A and B as determined by SDS PAGE under non-reducing conditions were found to be 58,000 and 29,000, respectively. The protein in peak A is thus two times the size of that in peak B. Both fractions interacted with swine anti-FMDV antibodies in the Western blot. Edman sequencing confirmed the identity of the first 10 amino acid residues of rVP1 in both peaks.

Under reducing conditions, most of rVP1 in peak A disappeared and moved to peak B position. When rVP1 in peak B was oxidized by $Cu^{+2}$-catalyzed $K_3Fe(CN)_6$ oxidation (Graceffa (1989) Biochemistry 28: 1282-1287) and then rechromatographed on a Superdex-200 column, most of the rVP1 was eluted in peak A fraction. These results suggest that peak A is a dimeric rVP1 linked by an intermolecular disulfide bond between two rVP1 monomers.

Thermal Influence on the Antigenicity of rVP1

The capability of monomeric rVP1 to interact with swine anti-rVP1 antibodies decreased when it was pretreated at 48° C. for 30 min. More than 70% of the monomeric rVP1 antigenicity was lost when the temperature treatment was raised above 66° C. In comparison, only about 50% of the dimeric rVP1 antigenicity was lost during the same heat treatment. These results suggest that rVP1 dimer is in a more thermal-stable conformation than the monomeric form.

Elicitation of Antibody Responses by rVP1 in Swine

ELISA showed that immunization of swine with rVP1 dimer (swine No. 545-548) and monomer (swine No. 553-556) elicited not only anti-rVP1 antibodies but also antibodies that reacted with P-29 (corresponding to amino acid residues 131-159 of VP1) (Table 1). There was no significant difference between rVP1 monomer and dimer in terms of their ability in eliciting anti-rVP1 or anti-P-29 antibody responses (P>0.1). To prevent conversion of monomer to dimer and vice versa due to reduction and oxidation processes in vivo, rVP1 was S-carboxymethylated. Table 1 shows that swine (No. 549-552) immunized with S-carboxymethylated rVP1 also elicited antibodies against rVP1 and P-29, respectively. Its anti-rVP1 antibody titer was slightly higher than that of rVP1 monomer and dimer while anti-P-29 titer was slightly lower, but the differences were not significant (P>0.1).

TABLE 1

Effect of dimeric and monomeric as well as S-carboxymethylated (CM-monomer) rVP1 in eliciting antibody responses and protection against FMDV

| Antigen | Swine number | Anti-rVP1 antibody titer ($\log_{10}$) | Anti-P-29 antibody titer ($\log_{10}$) | Neutralizing antibody titer ($\log_{10}$) | Protection[a] |
|---|---|---|---|---|---|
| rVP1 dimer | 545 | 4.48 | 2.34 | <0.48 | P |
|  | 546 | 5.66 | 3.60 | 1.51 | P |
|  | 547 | 5.26 | 3.48 | 1.65 | P |
|  | 548 | 5.20 | 2.65 | 1.96 | P |
|  | Average | 5.31 | 3.28 | 1.63 | 100% P |
| CM-monomer | 549 | 5.36 | 2.81 | 1.51 | P |
|  | 550 | 5.93 | 3.18 | 0.90 | PP* |
|  | 551 | 4.93 | 2.18 | <0.48 | P |
|  | 552 | 5.71 | 3.53 | 0.90 | P |
|  | Average | 5.62 | 3.15 | 1.09 | 75% P |
| rVP1 monomer | 553 | 5.45 | 4.08 | 2.26 | P |
|  | 554 | 5.81 | 2.70 | <0.48 | P |
|  | 555 | 4.78 | 3.45 | 1.20 | P |
|  | 556 | 5.39 | 3.11 | 1.65 | P |
|  | Average | 5.49 | 3.62 | 1.78 | 100% P |
| Buffer Control | 557 | <1 | <1 | <0.48 | NP |
|  | 558 | <1 | <1 | <0.48 | NP |
|  | Average | <1 | <1 | <0.48 | 0% P |

[a]NP: Not protected; P: protected, no symptom was detected; PP: partially protected, one small blister on the right back leg.

Elicitation of Neutralizing Antibody and Protection Against FMD Challenge in Swine Both monomeric and dimeric rVP1 induced neutralizing antibodies in three out of four animals (Table 1), while negative controls did not. Viral challenge studies revealed that all four swine immunized by either monomeric or dimeric rVP1 were fully symptom free (Table 1), whereas the negative controls were not protected. Immunization of swine with S-carboxymethylated rVP1 monomer (CM-monomer) also induced neutralizing antibodies in three out of four animals. The average neutralizing titer of those immunized with CM-monomer ($\log_{10}$ mean=1.09) was slightly lower than those immunized with rVP1 dimer ($\log_{10}$ mean=1.63) or rVP1 monomer ($\log_{10}$ mean=1.78), but the difference was not statistically significant (P>0.1). Viral challenge experiment showed that three out of four CM-monomer immunized swine were protected while one was only partially protected. These results suggest that both monomeric and dimeric rVP1 are useful for vaccinating swine against FMDV.

T Cell Response of Swine to rVP1

T cells, isolated from the blood of all test groups of swine, were stimulated in vitro with 5, 10 and 20 μg/ml of rVP1, respectively. Best response was obtained when T cells of vaccinated swine were stimulated with 10 μg/ml of rVP1. No T cell proliferative response was found in the negative control group while those vaccinated swine that exhibited neutralizing antibody titer all showed a significant proliferative response (Table 2; P<0.05). Interestingly, T cells from the three swine that were protected against FMD challenge with undetectable neutralizing antibody titer (swine No. 545, 551, and 554) also showed proliferative response, whereas those from the swine that was partially protected (swine No. 550) exhibited the lowest response among all the vaccinated swine.

TABLE 2

In vitro proliferative response of T cells obtained from swine injected with buffer solution, dimeric, monomeric, and S-carboxymethylated (CM-monomer) rVP1, respectively

| Antigen | Swine Number | Stimulation[a] Index | Mean ± S.D. |
|---|---|---|---|
| rVP1 dimer | 545 | 2.0 | 2.0 ± 0.14 |
|  | 546 | 1.8 |  |
|  | 547 | 2.1 |  |
|  | 548 | 2.1 |  |
| CM-monomer | 549 | 1.5 | 1.58 ± 0.22 |
|  | 550 | 1.3 |  |
|  | 551 | 1.7 |  |
|  | 552 | 1.8 |  |
| rVP1 monomer | 553 | 1.4 | 1.58 ± 0.13 |
|  | 554 | 1.6 |  |
|  | 555 | 1.6 |  |
|  | 556 | 1.7 |  |
| Buffer Control | 557 | 1.0 | 1.05 |
|  | 558 | 1.1 |  |

[a]Proliferative response was determined by in vitro simulation of swine T cells with 10 μg/ml of rVP1 monomer. Stimulation Index: mean absorbance of culture with rVP1 stimulation/mean absorbance of culture without rVP1 stimulation.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and

What is claimed is:

1. A method of producing a water-soluble polypeptide, the method comprising:

unfolding a water-insoluble polypeptide that contains one or more monomers of a VP1 protein of a foot-and-mouth disease virus in a first solution containing urea, and refolding the polypeptide, thereby producing a water-soluble polypeptide, wherein the refolding step includes treating the polypeptide in a second solution containing sodium dodecyl sulfate followed by gel filtration column chromatography.

2. The method of claim 1, wherein the second solution contains 1% sodium dodecyl sulfate.

3. A method of producing a polypeptide, the method comprising:

expressing in a cell a water-insoluble polypeptide that contains two or more monomers of a VP1 protein of a foot-and-mouth disease virus, collecting the polypeptide from the cell, unfolding the polypeptide in a first solution containing urea, and refolding the polypeptide, thereby producing a water-soluble polypeptide, wherein the refolding step includes treating the polypeptide in a second solution containing sodium dodecyl sulfate followed by gel filtration column chromatography.

4. The method of claim 3, wherein the second solution contains 1% sodium dodecyl sulfate.

* * * * *

SEQUENCE LISTING

<160> NUMBER OF SEQ ID NOS: 6

<210> SEQ ID NO 1
<211> LENGTH: 705
<212> TYPE: DNA
<213> ORGANISM: Homo sapiens

<400> SEQUENCE: 1

```
atggctagca tgactggtgg acagcaaatg ggtcgcggat ccaccacctc tgcgggtgag      60
tctgcggacc ccgtgactgc caccgtcgag aactacggtg gtgagacaca agtccagagg     120
cgccagcaca cggacagtgc gttcatattg gacaggttcg tgaaagtcaa gccaaaggaa     180
caagttaatg tgttggacct gatgcagatc cctgcccaca ccttggtagg ggcgctcctg     240
cgaacggcca cctactactt ctctgacctg gagctggccg tcaagcacga gggcgatctc     300
acctgggtcc caaacggcgc ccctgagaca gcactggaca cactaccaa cccaacagct      360
taccacaagg aacccctcac acggctggcg ctgccttaca cggctccaca ccgtgtctta     420
gcgaccgtct acaacgggag cagtaagtac ggtgacacca gcactaacaa cgtgagaggt     480
gaccttcaag tgttagctca gaaggcagaa agaactctgc ctacctcctt caacttcggt     540
gccatcaagg caactcgtgt tactgaacta ctctacagaa tgaagagagc cgagacatac     600
tgtcccaggc cccttctcgc cattcaaccg agtgacgcta gacacaagca gaggattgtg     660
gcacccgcaa acagcttcct gctcgagcac caccaccacc accac                     705
```

<210> SEQ ID NO 2
<211> LENGTH: 235
<212> TYPE: PRT
<213> ORGANISM: Homo sapiens

<400> SEQUENCE: 2

```
Met Ala Ser Met Thr Gly Gly Gln Gln Met Gly Arg Gly Ser Thr Thr
  1               5                  10                  15

Ser Ala Gly Glu Ser Ala Asp Pro Val Thr Ala Thr Val Glu Asn Tyr
             20                  25                  30

Gly Gly Glu Thr Gln Val Gln Arg Arg Gln His Thr Asp Ser Ala Phe
         35                  40                  45

Ile Leu Asp Arg Phe Val Lys Val Lys Pro Lys Glu Gln Val Asn Val
 50                  55                  60

Leu Asp Leu Met Gln Ile Pro Ala His Thr Leu Val Gly Ala Leu Leu
 65                  70                  75                  80

Arg Thr Ala Thr Tyr Tyr Phe Ser Asp Leu Glu Leu Ala Val Lys His
                 85                  90                  95

Glu Gly Asp Leu Thr Trp Val Pro Asn Gly Ala Pro Glu Thr Ala Leu
            100                 105                 110

Asp Asn Thr Thr Asn Pro Thr Ala Tyr His Lys Glu Pro Leu Thr Arg
        115                 120                 125

Leu Ala Leu Pro Tyr Thr Ala Pro His Arg Val Leu Ala Thr Val Tyr
    130                 135                 140

Asn Gly Ser Ser Lys Tyr Gly Asp Thr Ser Thr Asn Asn Val Arg Gly
145                 150                 155                 160

Asp Leu Gln Val Leu Ala Gln Lys Ala Glu Arg Thr Leu Pro Thr Ser
                165                 170                 175

Phe Asn Phe Gly Ala Ile Lys Ala Thr Arg Val Thr Glu Leu Leu Tyr
            180                 185                 190
```

```
Arg Met Lys Arg Ala Glu Thr Tyr Cys Pro Arg Pro Leu Leu Ala Ile
        195                 200                 205

Gln Pro Ser Asp Ala Arg His Lys Gln Arg Ile Val Ala Pro Ala Lys
        210                 215                 220

Gln Leu Leu Leu Glu His His His His His His
225                 230                 235

<210> SEQ ID NO 3
<211> LENGTH: 705
<212> TYPE: DNA
<213> ORGANISM: Homo sapiens

<400> SEQUENCE: 3
gtggtggtgg tggtggtgct cgagcagaag ctgttttgcg ggtgccacaa tcctctgctt      60
gtgtctagcg tcactcggtt gaatggcgag aaggggcctg ggacagtatg tctcggctct    120
cttcattctg tagagtagtt cagtaacacg agttgccttg atggcaccga agttgaagga    180
ggtaggcaga gttctttctg ccttctgagc taacacttga aggtcacctc tcacgttgtt    240
agtgctggtg tcaccgtact tactgctccc gttgtagacg tcgctaaga cacggtgtgg     300 agccgtgtaa ggcagcgcca gccgtgtgag gggttccttg tggtaagctg ttgggttggt    360
agtgttgtcc agtgctgtct caggggcgcc gtttgggacc caggtgagat cgccctcgtg    420
cttgacggcc agctccaggt cagagaagta gtaggtggcc gttcgcagga gcgcccctac    480
caaggtgtgg gcagggatct gcatcaggtc aacacattaa acttgttcct ttggcttgac    540
tttcacgaac ctgtccaata tgaacgcact gtccgtgtgc tggcgcctct ggacttgtgt    600
ctcaccaccg tagttctcga cggtggcagt cacggggtcc gcagactcac ccgcagaggt    660
ggtggatccg cgacccattt gctgtccacc agtcatgcta gccat                    705

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
gtgatgctcg agcagaagct gttttgcggg t                                    31

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
ccgggatcca ccacctctgc gggtgact                                        28

<210> SEQ ID NO 6
<211> LENGTH: 29
<212> TYPE: PRT
<213> ORGANISM: Artificial Sequence
<220> FEATURE:
<223> OTHER INFORMATION: Synthetically generated peptide
```

-continued

```
<400> SEQUENCE: 6

Asn Gly Ser Ser Lys Tyr Gly Asp Thr Ser Thr Asn Asn Val Arg Gly
 1               5                   10                  15

Asp Leu Gln Val Leu Ala Gln Lys Ala Glu Arg Thr Leu
            20                  25
```